United States Patent [19]
Flanagan

[11] 4,391,773
[45] Jul. 5, 1983

[54] METHOD OF PURIFYING AIR AND NEGATIVE FIELD GENERATOR

[76] Inventor: G. Patrick Flanagan, 9989 E. Morrill Way, Tucson, Ariz. 85715

[21] Appl. No.: 271,132

[22] Filed: Jun. 8, 1981

[51] Int. Cl.³ .............................................. A61L 2/00
[52] U.S. Cl. ......................................... 422/22; 55/2; 55/123; 55/155; 55/279; 361/235; 422/121
[58] Field of Search ...................... 55/2, 123, 155, 146, 55/150, 279; 422/22, 23, 121; 361/231, 232, 235

[56] References Cited

U.S. PATENT DOCUMENTS

| | | | |
|---|---|---|---|
| 2,085,735 | 7/1937 | Brion | 55/150 |
| 3,654,534 | 4/1972 | Fischer | 361/231 |
| 3,898,468 | 8/1975 | Guerin | 55/139 |
| 4,037,268 | 7/1977 | Gallagher | 55/150 |
| 4,096,544 | 6/1978 | Ignatjev | 361/231 |

Primary Examiner—Bernard Nozick
Attorney, Agent, or Firm—Edmond T. Patnaude

[57] ABSTRACT

A housing encloses a high voltage, high frequency power supply having output terminals connected to a pair of electrodes mounted on opposite sides of a solid dielectric, the electrodes and solid dielectric being encapsulated in an insulator and mounted in a tunnel in the housing, the air to be purified being circulated through the tunnel.

8 Claims, 3 Drawing Figures

METHOD OF PURIFYING AIR AND NEGATIVE FIELD GENERATOR

The present invention relates to a new and improved method and apparatus for generating a negative electric field of sufficient intensity to purify air, and it also relates to the discovery of a strong negative field surrounding a dielectric capacitor connected across a high frequency, high voltage source of energy.

BACKGROUND OF THE INVENTION

It is well known that odors, dust particles, bacteria and the like can be removed from air by subjecting the air and entrained material to a negative field. For example, U.S. Pat. No. 4,037,268 describes a system for developing a negative charge effect by generating a plasma between sets of anode and cathode electrodes and using this effect to purify air. Also, ozone generators have been used to develop a negatively charged field for neutralizing the normal positive charge on airborne dust particles and the like. Some ozone generators have employed a gas discharge while others have used ultraviolet light for ozonating air. It would be desirable however, to provide a generator which would develop a negative field in air without the use of a gaseous discharge or ultraviolet light and which would not produce ozone or other harmful contaminents, whereby the generator could be safely used to purify air.

SUMMARY OF THE INVENTION

Briefly, in accordance with the present invention there is developed a negative field of sufficient intensity to purify air by neutralizing airborne particles and for killing airborne bacteria. This strong negative field is generated by applying a high voltage, high frequency source of alternating electric energy across a solid dielectric. I have found that a high intensity negative field is thus developed in the air surrounding the dielectric. This negative field has been observed to precipate airborne solids from the surrounding air, and to retard, if not prevent, the growth of bacterial on organic matter disposed within about fifty centimeters of the generator. Also, moisture is removed from the air in the vicinity of the generator by this strong negative field.

In an air purifier embodying the present invention the negative field generator is mounted in a tunnel through which the air to be purified is circulated.

GENERAL DESCRIPTION OF THE DRAWING

The present invention will be better understood by a reading of the following detailed description taken in connection with the accompanying drawing wherein.

DETAILED DESCRIPTION OF THE INVENTION

Figure 1:
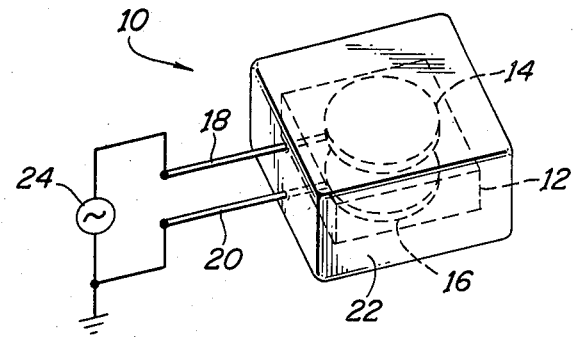
FIG. 1 is a perspective view of a negative field generator device operatively connected to a high frequency, high voltage source of power, the latter being shown in schematic form.

Referring to FIG. 1, a negative field generator 10 embodying the present invention comprises a rectangular sheet 12 of a solid dielectric material such as glass or plastic, such as acrylic, to the opposite faces of which are directly mounted a pair of thin circular metallic electrodes 14 and 16. It may be seen from inspection of the drawing that the peripheral edges of electrodes 14 and 16 are spaced a substantial distance from the adjacent edges of the sheet 12. As more fully explained hereinafter, this spacing is made sufficient to prevent arcing between the electrodes wherefor the spacing depends on the voltage to be applied between the electrodes 14 and 16.

A pair of conductive leads 18 and 20 are respectively connected to the electrodes 14 and 16 and extend outwardly from a block 22 of an insulating material in which the assembly of the electrodes 14 and 16 and the sheet 14 is encapsulated to provide a completely solid unit. The leads 18 and 20 are respectively connected to the output terminals of an electric power source 24 of high voltage, high frequency energy. The power source 24 may be a conventional oscillator having, for example, an output of 24 kilovolts at a frequency of 38 kiloHertz. When using such a source of power, arcing must be prevented. Arcing can be prevented by using a sheet 12 of acrylic having a thickness of 0.4 inch with three inch diameter electrodes 14 and 16 spaced a minimum of one-half inch from the closest edges of the sheet 12. It is important that the applied voltage be less than the breakdown voltage of the dielectric sheet and of the air or other gas surrounding the unit. A strong negative field of toroidal configuration is generated by the system shown in FIG. 1 and has been found to produce a sufficiently strong field at a distance of fifty centimeters from the unit for removing entrained impurities from the air surrounding the unit.

Figure 2:
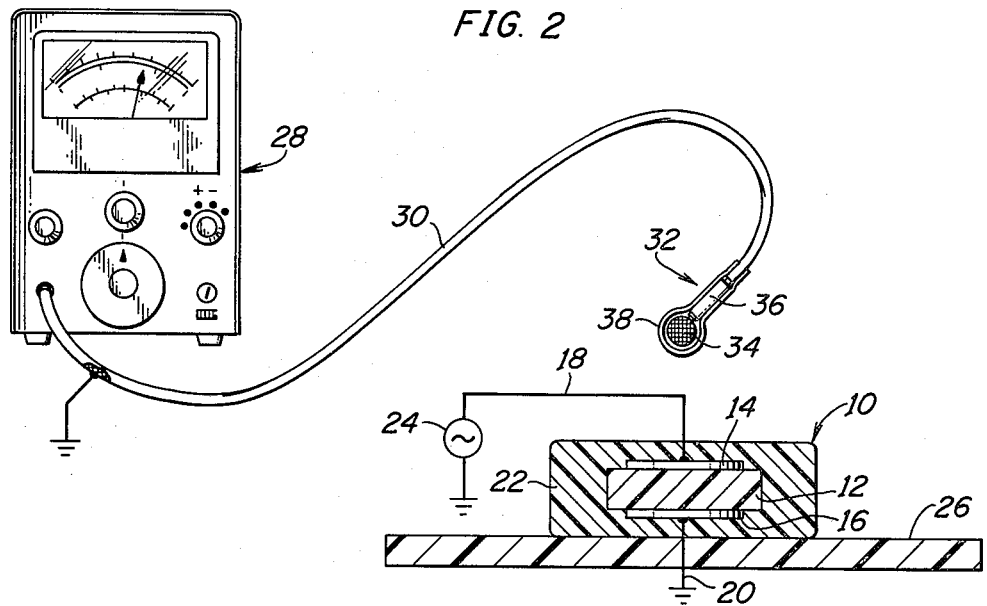
FIG. 2 is a schematic view showing the manner, in which the negative electric field surrounding a generator embodying the present invention has been measured.

Referring to FIG. 2, there is shown the test set-up which was used to measure the strength of the negative electric field developed around the generator 10. The device 10 was placed on an insulating surface 26 and energized from a high voltage, high frequency power source 24. The input terminals of an electrometer 28 were connected by a shielded cable 30 to an ion current probe 32 of the type designed by J. C. Beckett and shown on page 362 of the issue of THE JOURNAL OF GENERAL PHYSIOLOGY, published on Nov. 20, 1957. The probe 32 comprises a conductive disc 34 which is connected to the central conductor in the cable 30. The connection from the disc 34 extends through cylindrical insulator 36 and a conductive wire 38 which is electrically connected to the grounded shield of the cable 30 lies in the plane of the disc 34 and surrounds it. The electrometer 28 thus measures the negative ion or electron field at the location of the disc 34. When a power source having a voltage of 24 kilovolts at a frequency of 38 kiloHertz was used, readings as high as $6.38 \times 10^{13}$ ions per $CM^2$ were measured at a distance of 50 cm. from the device 10. This negative field is sufficiently strong to purify air by discharging particulates entrained therein and to destroy bacteria in the air. An input voltage of 5 kilovolts at a frequency of about 20 kiloHertz produced a negative field which appears to have about the minimum strength for purifying air. The measured field strength at 50 cm., from the device was 500,000 ions per $CM^2$ per second.

Figure 3:
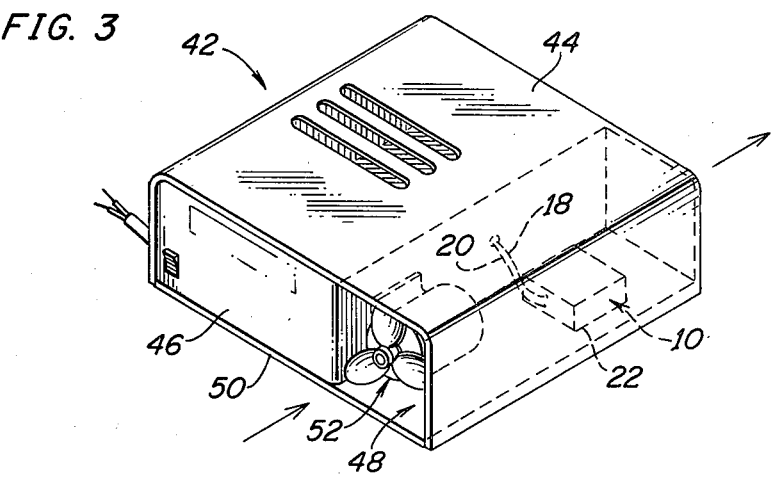
FIG. 3 is a perspective view of an air purifier embodying the present invention.

Referring to FIG. 3, there is shown an air purifying device 42 embodying the present invention. The device 42 comprises a housing 44 in which is mounted an electronic control unit 46 including a high voltage, high frequency power supply. A passageway or tunnel 48 is provided at one side of the power supply and except for its open ends is entirely surrounded by grounded metallic members. In this case, the outer housing including the base portion 50 which is metal and is grounded during operation of the unit. A low velocity electric fan of the whisper type is mounted to the vertical wall of the control unit 46 adjacent one end of the tunnel 48 and causes the ambient air to flow from left to right through the unit as shown in FIG. 3. Mounted to the floor 50 on the downstream side of the fan 52 is a negative field generating unit 10 as described hereinabove in connection with FIG. 1. The negative field is confined within the tunnel 48 and purifies or otherwise treats the air or gas flowing through the negative electric field produced therein.

The electric field which is developed around the unit 10 is negative and because of the fact that the unit is energized from an alternating source of energy the field may be expanding and contracting at twice the frequency of the power supply 24. However, the inertia of the electrometer, and particularly the needle thereof, would be unable to respond to such high frequency variations and does in fact indicate a constant negative field surrounding the device 10.

While the present invention has been described in connection with particular embodiments thereof, it will be understood by those skilled in the art that many changes and modifications may be made without departing from the true spirit and scope of the present invention. Therefore, it is intended by the appended claims to cover all such changes and modifications which come within the true spirit and scope of this invention.

What is claimed:
1. A method of purifying air, comprising the steps of
   placing in proximity to said air a capacitor including a pair of electrodes spaced apart by a solid dielectric material, and
   applying between said electrodes an A.C. voltage of at least about 5000 volts having a frequency of at least twenty kiloHertz, said voltage being less than the breakdown voltage across said electrodes.
2. A method according to claim 1, comprising the further step of
   circulating the air to be purified through a space within fifty centermeters of said capacitor.
3. A method according to claim 1, wherein
   said dielectric is a sheet of dielectric material, and
   said electrodes are generally planar conductive members.
4. A method according to claim 3, wherein said sheet of dielectric material is acrylic resin.
5. Apparatus for generating a negative field in a gas, comprising
   a solid, dielectric sheet,
   first and second metallic electrodes respectively mounted in mutually parallel relationship to opposite sides of said dielectric sheet,
   a body of insulating material completely enclosing said electrodes and said dielectric sheet to prevent any arcing between said electrodes, and
   means for connecting a high voltage, high frequency source between said electrodes.
6. Apparatus according to claim 5, wherein
   said source has a voltage of 5000 volts or more and a frequency of twenty kiloHertz or more.
7. Apparatus according to claim 5 comprising
   passageway means defining a passageway,
   said electrodes, said dielectric sheet and said body of insulating material being mounted within said passageway, and
   blower means for causing said air to flow through said passageway.
8. Apparatus according to claim 7 comprising
   housing means in which said source is mounted and which includes said passageway means.

* * * * *